(12) United States Patent
Inoue et al.

(10) Patent No.: US 10,034,489 B2
(45) Date of Patent: Jul. 31, 2018

(54) METHOD FOR PRODUCING LIQUID FOOD COMPOSITION

(71) Applicant: KANEKA CORPORATION, Osaka-shi (JP)

(72) Inventors: Hiroaki Inoue, Takasago (JP); Masao Sato, Takasago (JP); Tadashi Moroshima, Takasago (JP); Ken Uekita, Takasago (JP); Shinichi Yokota, Takasago (JP); Yui Kawashima, Shinagawa-ku (JP); Tadaaki Hashimoto, Shinagawa-ku (JP); Kazuya Hamada, Takasago (JP)

(73) Assignee: Kaneka Corporation, Osaka-shi (JP)

( * ) Notice: Subject to any disclaimer, the term of this patent is extended or adjusted under 35 U.S.C. 154(b) by 0 days.

(21) Appl. No.: 14/897,394

(22) PCT Filed: Jun. 13, 2014

(86) PCT No.: PCT/JP2014/065679
§ 371 (c)(1),
(2) Date: Dec. 10, 2015

(87) PCT Pub. No.: WO2014/200079
PCT Pub. Date: Dec. 18, 2014

(65) Prior Publication Data
US 2016/0143330 A1   May 26, 2016

(30) Foreign Application Priority Data
Jun. 14, 2013   (JP) ................. 2013-125292

(51) Int. Cl.
| | |
|---|---|
| A23L 2/38 | (2006.01) |
| A23L 2/52 | (2006.01) |
| A23L 33/16 | (2016.01) |
| A23L 1/29 | (2006.01) |
| A23L 2/66 | (2006.01) |
| A23L 33/00 | (2016.01) |
| A23L 33/10 | (2016.01) |
| A23L 33/17 | (2016.01) |
| A23L 33/21 | (2016.01) |

(52) U.S. Cl.
CPC ............ *A23L 1/296* (2013.01); *A23L 2/38* (2013.01); *A23L 2/52* (2013.01); *A23L 2/66* (2013.01); *A23L 33/10* (2016.08); *A23L 33/16* (2016.08); *A23L 33/17* (2016.08); *A23L 33/21* (2016.08); *A23L 33/40* (2016.08); *A23V 2002/00* (2013.01)

(58) Field of Classification Search
CPC ............ A23L 2/66; A23L 33/16; A23L 33/40
See application file for complete search history.

(56) References Cited

U.S. PATENT DOCUMENTS

| | | | | | |
|---|---|---|---|---|---|
| 4,786,510 | A | * | 11/1988 | Nakel | A23L 2/52 424/648 |
| 6,024,994 | A | * | 2/2000 | Jacobson | A23L 33/165 426/573 |
| 6,241,996 | B1 | * | 6/2001 | Hahn | A23L 33/185 424/439 |
| 6,261,610 | B1 | * | 7/2001 | Sher | A23L 33/165 426/573 |
| 6,458,395 | B1 | * | 10/2002 | Emoto | A23L 33/17 426/573 |
| 6,569,477 | B2 | * | 5/2003 | Lederman | A23G 3/346 426/443 |
| 2001/0007673 | A1 | * | 7/2001 | Goldenberg | A61K 9/0019 424/400 |
| 2002/0193344 | A1 | * | 12/2002 | Wolf | A61K 31/715 514/54 |
| 2003/0118712 | A1 | | 6/2003 | Navarro Y Koren et al. | |
| 2003/0134027 | A1 | * | 7/2003 | Te Hennepe | A23L 2/52 426/590 |
| 2007/0087038 | A1 | * | 4/2007 | Richardson | A61K 9/0065 424/439 |
| 2007/0196539 | A1 | | 8/2007 | Yang et al. | |
| 2008/0268102 | A1 | * | 10/2008 | Mellema | A23C 11/103 426/74 |
| 2010/0143573 | A1 | * | 6/2010 | Godber | A23L 2/52 426/648 |
| 2013/0172245 | A1 | | 6/2013 | Inoue et al. | |
| 2015/0044290 | A1 | * | 2/2015 | Inoue | A61K 9/0065 424/489 |
| 2016/0143331 | A1 | * | 5/2016 | Inoue | A61K 31/716 514/5.5 |

FOREIGN PATENT DOCUMENTS

| | | |
|---|---|---|
| JP | 7-284383 | 10/1995 |
| JP | 10-136940 | 5/1998 |
| JP | 2000-83595 | 3/2000 |
| JP | 2005-513077 | 5/2005 |
| JP | 2006-182767 | 7/2006 |

(Continued)

OTHER PUBLICATIONS

International Search Report dated Sep. 9, 2014 in PCT/JP2014/065679.

(Continued)

*Primary Examiner* — Michele L Jacobson
(74) *Attorney, Agent, or Firm* — Oblon, McClelland, Maier & Neustadt, L.L.P.

(57) ABSTRACT

A liquid food composition that can be conveniently ingested or given with a tube and contains reduced aggregates in the composition is provided. A liquid food composition that shows fluidity in the neutral region, but solidifies in the stomach environment is further provided. According to the production method of the present invention, generation of fine particles in the production process of a liquid food composition containing a divalent metal salt, a protein, and water-soluble dietary fibers is reduced. Therefore, emulsification stability of the composition is improved, clogging of aggregates in strainer disposed in the production line etc. are eliminated, and thus the composition can be efficiently produced. Furthermore, since the composition obtained by the production method shows fluidity in the neutral region, but solidifies in the stomach environment, it can be conveniently ingested or given with a tube, and can effectively reduce the risks for developing gastroesophageal reflux disease, aspiration pneumonia, diarrhea, etc.

16 Claims, No Drawings

(56) References Cited

FOREIGN PATENT DOCUMENTS

| | | |
|---|---|---|
| JP | 2007-176848 | 7/2007 |
| JP | 2008-301723 | 12/2008 |
| JP | 2009-153392 | 7/2009 |
| JP | 2009-524575 | 7/2009 |
| JP | 2009-527252 | 7/2009 |
| WO | WO 03/053165 A1 | 7/2003 |
| WO | WO 2007/039294 A2 | 4/2007 |
| WO | WO 2007/039294 A3 | 4/2007 |
| WO | WO 2007/098092 A2 | 8/2007 |
| WO | WO 2011/074670 A1 | 6/2011 |

OTHER PUBLICATIONS

International Preliminary Report on Patentability dated Dec. 23, 2015 in PCT/JP2014/065679 filed Jun. 13, 2014 (with English translation).

International Preliminary Report on Patentability and Written Opinion dated Dec. 23, 2015 in PCT/JP2014/065679 filed Jun. 13, 2014 (English translation only).

* cited by examiner

METHOD FOR PRODUCING LIQUID FOOD COMPOSITION

TECHNICAL FIELD

The present invention relates to a method for producing a liquid food composition containing a salt of a divalent metal such as calcium and magnesium, a protein derived from milk, soybean, etc., and water-soluble dietary fibers such as sodium alginate and pectin.

BACKGROUND ART

In recent years, nutritious foods containing minerals etc., which tend to be insufficient for people of today, and produced in consideration of nutritional balance attract attention. They are used not only as conveniently ingestible takeout foods and diet foods, but also as liquid foods for ingestion of nutrition by those who suffer from difficulty in oral ingestion of foods due to advanced age, disease, wound or disability. However, since many of liquid foods are those of low viscosity fluid type, they pose problems of developing gastroesophageal reflux disease, aspiration pneumonia, vomiting, diarrhea, etc. As means for solving such problems, there have been disclosed a method of giving a preliminarily gelled nutritious food (Patent document 1), a method of adding a gelling agent to a nutritious food at the time of ingestion of the food to reduce fluidity of the nutritious food in the stomach (Patent document 2), and a composition containing a polysaccharide, a mineral, and a gas-forming component, which is gelled under the endogastric condition (Patent document 3).

As for other foods, there have been proposed methods of adding phosphoric acid or an organic acid etc. to foods for suppressing aggregation and precipitation of proteins and divalent metal salts (refer to, for example, Patent documents 4 and 5)

PRIOR ART REFERENCES

Patent Documents

Patent document 1: Japanese Patent Unexamined Publication (KOKAI) No. 2006-182767
Patent document 2: Japanese Patent Unexamined Publication (KOKAI) No. 2007-176848
Patent document 3: Japanese Patent Unexamined Publication (KOHYO) No. 2009-524575
Patent document 4: Japanese Patent Unexamined Publication (KOKAI) No. 2000-83595
Patent document 5: Japanese Patent Unexamined Publication (KOKAI) No. 10-136940

SUMMARY OF THE INVENTION

Object to be Achieved by the Invention

However, for example, the method described in Patent document 1 has a characteristic that the reduced fluidity of the nutritious food makes it difficult to pass the nutritious food through a tube at the time of tube feeding. Therefore, it has problems, for example, ingestion of nutritious foods takes a long time, which results in burden on persons who ingest them, or causes development and aggravation of bedsore due to continuance of seating position. The method described in Patent document 2 requires separate addition of a gelling agent to nutritious foods, and it makes the operation more complicated. Therefore, at the time of using a nutritious food, the preparation of the nutritious food requires labor and time, and risks are also expected in view of sanitation concerning, for example, contamination with bacteria during the operation. The composition described in Patent document 3 can be expected to show an effect of ameliorating the aforementioned problems to a certain extent, but since the composition contains a protein, a divalent metal salt, and water-soluble dietary fibers, it suffers from a problem that aggregation and precipitation caused after a heat sterilization treatment reduce the quality of product.

In order to solve the problem of the composition of Patent document 3, the inventors of the present invention examined a method of adding phosphoric acid or an organic acid to a solution containing proteins, and then adding a divalent metal salt to the solution as described in, for example, Patent document 4. However, a lot of aggregates were generated, and the quality was deteriorated. Further, the following method was also examined. That is, as described in Patent document 5, warmed water, an emulsifier, and oil were added to a first vessel, and preliminarily emulsified, and then casein sodium (protein) and other raw materials were added to the emulsion, and dissolved by stirring. Further, calcium carbonate, calcium chloride, citric acid, and sodium citrate were added to a second vessel in this order, the mixture was stirred for 3 minutes, and complete dissolution was confirmed. Then, water-soluble calcium chloride, water-soluble calcium glycerate, and potassium carbonate were added to the solution, and dissolved by stirring. Furthermore, vitamins (multiple vitamin preparation) were added to water in a third vessel, and dissolved, a flavoring agent was added and dissolved, and finally the contents of the first and second vessels were added to the third vessel. However, when water-soluble dietary fibers were further added, viscosity of the composition in the vessel sharply increased, and any liquid food composition could not be obtained.

In view of the aforementioned problems, an object of the present invention is to provide a liquid food composition that can be conveniently ingested and given with a tube, and contains reduced aggregates in the composition. Another object of the present invention is to provide a liquid food composition that shows fluidity in the neutral region, but solidifies in the stomach environment.

Means for Achieving the Object

The inventors of the present invention further conducted various researches, as a result, found that, when a composition containing a divalent metal salt, a phosphoric acid salt and/or an organic acid salt, a protein, and water-soluble dietary fibers was produced, the aforementioned problems could be solved by mixing the phosphoric acid salt and/or the organic acid salt with a solution containing the divalent metal salt until pH of the mixture reached a specific pH value, and then adding the protein and water-soluble dietary fibers to the obtained mixture, and thus accomplished the present invention.

The present invention is embodied as follows.
(1) A method for producing a liquid food composition containing a divalent metal salt, a phosphoric acid salt and/or an organic acid salt, a protein, and water-soluble dietary fibers, which comprises:
   (a) the step of adding the divalent metal salt to a solvent, then adding the phosphoric acid salt and/or the organic acid salt, and performing mixing until pH of the mixture becomes 6.2 to 9.5, (b) the step of adding the protein to the mixture obtained in the step (a), and
(c) the step of adding the water-soluble dietary fibers.
(2) The production method according to (1), wherein temperature of the mixture is 30 to 80° C. in the step (b).
(3) The production method according to (1) or (2), wherein mixing ratio of phosphate ions and/or organic acid ions derived from the phosphoric acid salt and/or the organic acid salt, and divalent metal ions derived from the divalent metal salt is not smaller than 0.5 and not larger than 12.
(4) The production method according to any one of (1) to (3), wherein 0.25 to 20 g/100 ml of the protein is added in the step (c).
(5) The production method according to any one of (1) to (4), wherein the divalent metal salt is a poorly-soluble divalent metal salt.
(6) The production method according to any one of (1) to (4), wherein the divalent metal salt is a calcium compound and/or a magnesium compound.
(7) The production method according to any one of (1) to (6), wherein the water-soluble dietary fibers consist of one or more kinds of fibers selected from the group consisting of alginic acid, a salt thereof, and pectin.

Effect of the Invention

According to the production method of the present invention, generation of fine particles can be reduced in the production process of a liquid food composition containing a divalent metal salt, a protein, and water-soluble dietary fibers, which improves emulsification stability of the composition, and eliminates clogging of fine particles and/or aggregates in a strainer disposed in the production line, and therefore the liquid food composition can be efficiently produced. Furthermore, since the composition obtained by the production method of the present invention shows fluidity in the neutral region, and solidifies in the stomach environment, it can be conveniently ingested or given via a tube, and can efficiently reduce the risks for developing gastroesophageal reflux disease, aspiration pneumonia, diarrhea, and so forth.

MODES FOR CARRYING OUT THE INVENTION

Hereafter, the present invention will be explained in detail.

The liquid food composition produced by the method of the present invention stably maintains the physical properties thereof as liquid at a pH not lower than 5.5 and not higher than 10.0, and when pH of the composition becomes lower than 5.5 in the stomach after ingestion, the form of the composition changes from liquid to solid. That is, the liquid food composition of the present invention is in the form of liquid at the time of production, distribution, preservation, ingestion thereof etc. Further, it has a property that when it is mixed with stomach juice after ingestion, the form thereof changes to solid. Therefore, the liquid food composition of the present invention does not require labor for separate addition of a gelling agent etc. at the time of ingestion, and it can be easily ingested also at the time of tube feeding, since it is liquid.

The term "liquid" or "properties as liquid" used in the present invention means a state of the liquid food composition that can be given via a tube (for example, a nasogastric tube, a gastrostomy tube). So long as the convenience for the tube feeding is not degraded, viscosity of the liquid food composition is not particularly limited, but the viscosity (25° C.) of the composition is preferably 1000 cP or lower, more preferably 500 cP or lower, further preferably 300 cP or lower, still further preferably 200 cP or lower. The viscosity referred to in the present invention is a viscosity value measured by the method described in the section of examples in this description, unless especially indicated.

The term "solidification" or "change (of the form) into solid" used for the liquid food composition produced according to the present invention means change of the properties of the liquid food composition as liquid under the acidic condition, such as insolubilization, increase in viscosity, solation, and gelation of the liquid food composition, and it can be evaluated with solidification ratio. The solidification ratio is an index for evaluating efficiency of the change of the form of the liquid food composition under the acidic condition in the stomach or the like. The liquid food composition showing a higher solidification ratio more efficiently solidifies or changes into solid, and leaves a smaller volume of liquid (unsolidified portion) in the stomach. The volume of liquid existing in the stomach is important for the various problems accompanying tube feeding, and according to the present invention, the solidification ratio is preferably higher than 51%, more preferably 56% or higher, further preferably 60% or higher, particularly preferably 65% or higher. If the solidification ratio is 51% or lower, the composition leaves a large volume of liquid (unsolidified portion) in the stomach, and development of gastroesophageal reflux disease, aspiration pneumonia, vomiting, diarrhea, and so forth may not be sufficiently suppressed. The solidification ratio referred to in the present invention is represented with a value measured by the method described in the section of examples, <Test for confirming solidification ratio> contained in this description.

The acidic condition referred to in the present invention means a condition of pH lower than 3.5, preferably pH 3.0 or lower, more preferably pH 2.5 or lower. The neutral condition referred to in the present invention means a condition of pH 3.5 to 12.5, preferably pH 3.5 or higher, more preferably pH 4.0 or higher, further preferably pH 4.5 or higher, particularly preferably pH 5.5 or higher, and preferably pH 12.5 or lower, more preferably pH 12.0 or lower, further preferably pH 11.5 or lower, particularly preferably pH 10.0 or lower.

The divalent metal salt referred to in the present invention is not particularly limit so long as a metal salt compound derived from calcium and/or magnesium is chosen. As for the metal salt compound derived from calcium, for example, such calcium compounds as calcium citrate, calcium carbonate, calcium dihydrogenpyrophosphate, tricalcium phosphate, calcium monohydrogenphosphate, calcium stearate, and calcium silicate are preferably used in view of suppression of thickening due to reaction with water-soluble dietary fibers. As for the metal salt compound derived from magnesium, for example, such magnesium compounds as magnesium carbonate, magnesium oxide, magnesium stearate, trimagnesium phosphate, and magnesium silicate are preferably used in view of suppression of thickening due to reaction with water-soluble dietary fibers. Among them, there are more preferably used calcium carbonate and magnesium carbonate, which are usable as food additives, and are divalent metal salts poorly-soluble under the neutral condition. These calcium compounds and/or magnesium compounds may be used independently, or as a combination of two or more kinds of them. The term "poorly-soluble"

referred to in the present invention means a property of from "Sparingly soluble" to "Practically insoluble" according to the solubility standards described in Japanese Pharmacopoeia, General Notices. More precisely, it means that when water containing a solute is vigorously shaken for 30 seconds every 5 minutes at 20±5° C., volume of water required for dissolving 1 g or 1 ml of the solute within 30 minutes is 30 ml or larger. Solubility of the poorly soluble calcium compound and/or poorly soluble magnesium compound used in the present invention at 20±5° C. and pH 7.0 is preferably 100 mg/100 ml or lower, more preferably 75 mg/100 ml or lower, further preferably 50 mg/100 ml or lower.

Amount of the divalent metal salt to be added is represented in terms of the amount of divalent metal ions derived from the divalent metal salt. From the viewpoint of supplementing mineral ingredients, the amount of the divalent metal salt (when two or more kinds of them are used in combination, total amount of them) in terms of divalent metal ions is preferably 1 mmol/l or larger, more preferably 10 mmol/l or larger, further preferably 15 mmol/l or larger, still further preferably 20 mmol/l or larger, particularly preferably 35 mmol/l or larger. Irrespective of the other conditions, the amount is preferably 1000 mmol/l or smaller, more preferably 500 mmol/l or smaller, further preferably 250 mmol/l or smaller, still further preferably 100 mmol/l or smaller, particularly preferably 65 mmol/l or smaller. An amount of divalent metal ions to be added smaller than 1 mmol/l is not preferred, since such an amount may develop mineral deficiency. Further, an amount of divalent metal ions to be added larger than 1000 mmol/l is not preferred, since clogging may be easily caused at the time of tube feeding of the liquid food composition.

The phosphoric acid salt and/or the organic acid salt used for the present invention is a raw material of which aqueous solution is not acidic when it is added to water or warm water, and it is not particularly limited so long as such a compound that suppresses generation of aggregation and precipitation due to reactions with proteins, divalent metal ions, water-soluble dietary fibers, etc. is chosen. Since pH of an aqueous solution dissolving an organic acid salt such as phosphoric acid salt and citric acid salt is in the range not lower than 3.5 and not higher than 12.5, organic acid salts are raw materials of which aqueous solutions are not acidic, and phosphoric acid and citric acid of which aqueous solutions show pH lower than 3.5 are excluded. For example, there are preferably used alkali metal salts and ammonium salts such as disodium hydrogenphosphate, dipotassium hydrogenphosphate, diammonium hydrogenphosphate, sodium dihydrogenphosphate, potassium dihydrogenphosphate, ammonium dihydrogenphosphate, trisodium phosphate, tripotassium phosphate, and triammonium phosphate, alkali metal salts and ammonium salts derived from pyrophosphoric acid, polyphosphoric acid, and metaphosphoric acid, alkali metal salts, alkaline earth metal salts, ammonium salts, etc. derived from organic acids such as acetic acid, lactic acid, citric acid, tartaric acid, malic acid, succinic acid, maleic acid, and fumaric acid. In view of more effectively suppressing generation of aggregation and precipitation resulting from reaction of proteins and divalent metal ions, use of phosphoric acid salt or citric acid salt is particularly preferred. These may be used independently or a combination of two or more kinds of them.

Amount of the phosphoric acid salt and/or the organic acid salt to be added is represented in terms of the amount of phosphate ions and/or organic acid ions derived from them. From the viewpoint of effectively suppressing generation of the aggregation and precipitation, the amount of the phosphoric acid salt and/or the organic acid salt (when two or more kinds of them are used in combination, total amount of them) in terms of phosphate ions and/or organic acid ions is preferably 2.5 mmol/l or larger, more preferably 5 mmol/l or larger, further preferably 10 mmol/l or larger, still further preferably 15 mmol/l or larger, particularly preferably 30 mmol/l or larger. Irrespective of the other conditions, the amount is preferably 150 mmol/l or smaller, more preferably 120 mmol/l or smaller, further preferably 100 mmol/l or smaller, still further preferably 80 mmol/l or smaller, particularly preferably 60 mmol/l or smaller. An amount of phosphate ions and/or organic acid ions smaller than 2.5 mmol/l, or larger than 150 mmol/l is not preferred, since generation of the aggregation and precipitation may not be effectively suppressed with such an amount.

The protein used in the present invention is not limited so long as an edible protein is chosen, and examples include animal proteins such as casein sodium, calcium casein, whey proteins, milk proteins, egg proteins, and albumen proteins, and vegetable proteins such as soybean proteins, green peas proteins, wheat proteins, rice proteins, and/or hydrolysates thereof. From the viewpoint of digestion of proteins, use of casein sodium, calcium casein, whey proteins, or soybean proteins is preferred, and as for soybean proteins, use of isolated soybean proteins, concentrated soybean proteins, etc. is more preferred. These proteins and/or hydrolysates may be used independently, or as a combination of two or more kinds of them.

Amount of the protein used in the present invention is not particularly limited so long as it is added in an amount nutritionally sufficient for a person who ingests or gives the composition, but as for the minimum amount of the protein (when two or more kinds of proteins are used in combination, total amount of them), the amount is preferably 0.25 g/100 ml or larger, more preferably 0.5 g/100 ml or larger, further preferably 1.0 g/100 ml or larger, still further preferably 2.0 g/100 ml or larger, particularly preferably 4.0 g/100 ml or larger. As for the maximum amount of the protein to be added, the amount is, irrespective of how the minimum amount is defined, preferably 20.0 g/100 ml or smaller, more preferably 10.0 g/100 ml or smaller, further preferably 7.5 g/100 ml or smaller, still further preferably 5.0 g/100 ml or smaller. An amount of the protein to be added smaller than 0.25 g/100 mL is not preferred in view of supplementation of protein components. An amount of the protein to be added larger than 20.0 g/100 mL is not preferred, since such an amount poses a problem of increase in viscosity of the composition.

In the present invention, one or more kinds of substances selected from the group consisting of alginic acid, a salt thereof, and pectin, and so forth can be used as water-soluble dietary fibers. As the salt of alginic acid, sodium salt, potassium salt, and ammonium salt are preferably used, and among them, sodium alginate is especially preferably used. As pectin, high-methoxylated (HM) pectin and low-methoxylated (LM) pectin are preferably used, and among them, LM-pectin is especially preferably used. Further, they can be used independently or as a combination of two or more kinds of them.

As for the minimum amount of the water-soluble dietary fibers to be added (when two or more kinds of them are used in combination, total amount of them), they are preferably used in an amount of 0.3 g/100 ml or larger, more preferably 0.5 g/100 ml or larger, further preferably in 0.7 g/100 ml or larger, particularly preferably 1.0 g/100 ml or larger. If the amount is less than 0.3 g/100 ml, solidification of the liquid food composition under the acidic condition may become insufficient. As for the maximum amount of the water-soluble dietary fibers to be added, they are preferably used in an amount of 5.0 g/100 ml or smaller, more preferably 2.5 g/100 ml or smaller, further preferably 2.0 g/100 ml or smaller, particularly preferably 1.5 g/100 ml or smaller, irrespective of how the minimum amount is defined. If the amount is larger than 5.0 g/100 ml, viscosity of the liquid food composition increases, and the properties thereof as liquid may be degraded.

The production method of the present invention comprises the step (a) of adding the divalent metal salt to a solvent, then adding the phosphoric acid salt and/or the organic acid salt, and performing mixing until pH of the mixture becomes 6.2 to 9.5.

In the present invention, the solvent is not particularly limited so long as a solvent usable for food is chosen, and water, warm water, cold water, ethanol, oil, and so forth can be used. Among them, water and warm water are especially preferably used from the viewpoint of efficient dispersion and/or dissolution of raw materials added to the composition.

In the present invention, the divalent metal salt may be contained in the solvent in a dissolved state or dispersed state. The divalent metal salt preferably exists in a state that it is dispersed in the solvent for efficiently providing the effect of the present invention. Further, the phosphoric acid salt and/or the organic acid salt used in the step (a) preferably exists in a dissolved state for effectively suppressing generation of fine particles during the production process.

To perform mixing until pH becomes 6.2 to 9.5 referred to in the present invention means to mix and/or homogenize an object until pH of the object becomes a predetermined pH by using a stirrer, emulsification machine, homogenizer, or the like. pH of the mixture containing the divalent metal salt, and the phosphoric acid salt and/or the organic acid salt changes during the mixing process. pH is preferably 6.2 or higher, more preferably 6.8 or higher, further preferably 7.0 or higher. As for the highest pH, pH is preferably 9.5 or lower, more preferably 9.0 or lower, irrespective of how the lowest pH is defined. When pH of the mixture under the preparation falls within the aforementioned pH range, it can be judged that the mixing step is completed. If pH of the mixture is lower than 6.2 in the step (a), the reaction of the divalent metal salt, and the phosphoric acid salt and/or the organic acid salt may not sufficiently advance, and aggregates may be generated after sterilization of the liquid food composition. If the pH is 3.5 or lower, when the water-soluble dietary fibers are added, viscosity of the composition sharply increases, and a liquid food composition cannot be obtained. Therefore, such a pH value is not preferred. Further, as for the highest pH, if pH exceeds 9.5, it prolongs the production time, and therefore such a pH value is not preferred. In the present invention, the mixing may be carried out before, during, or after the addition of the divalent metal salt, and the phosphoric acid salt and/or the organic acid salt, but it is preferably performed before addition of the divalent metal salt for effectively providing the effect of the present invention.

In addition, in the step (a), it is preferable to add the divalent metal salt to the solvent, and then add the phosphoric acid salt and/or the organic acid salt for suppressing generation of fine particles, which cause clogging of strainer. If the phosphoric acid salt and/or the organic acid salt is added to the solvent, and then the divalent metal salt is added, generation of fine particles cannot be effectively suppressed, and the strainer may be clogged. Therefore, such an operation is not preferred.

The production method of the present invention further comprises the step (b) of adding a protein to the mixture obtained in the step (a). The addition of a protein in the step (b) can be carried out by adding the protein to the mixture obtained after the step (a). It may also be carried out by adding a separately prepared slurry of the protein to the mixture, and mixing them (mixing and/or homogenization). The mixing in the step (b) can also be performed by using a stirrer, emulsification machine, homogenizer, or the like.

The production method of the present invention further comprises the step (c) of adding water-soluble dietary fibers. The addition of the water-soluble dietary fibers of the step (c) may be performed before, during, or after the step (a) or (b). For efficiently carrying out the mixing of the divalent metal salt, the phosphoric acid salt and/or the organic acid salt, and the protein, the addition of the water-soluble dietary fibers is preferably performed after the steps (a) and (b). The mixing of the step (c) can also be performed by using a stirrer, emulsification machine, homogenizer, or the like.

As described above, the order of the additions of the divalent metal salt, the phosphoric acid salt and/or the organic acid salt, and the protein in the steps (a) and (b), and control of the operation of adding the protein using pH as an index in the step (a) are important for the production method of the present invention, and according to the production method characterized by the specific features concerning the aforementioned factors, it becomes possible to obviate generation of clogging in the strainer, generation of clogging of strainer during the production process, and generation of aggregates derived from the protein, divalent metal ion, water-soluble dietary fibers, etc. after the sterilization can be more effectively suppressed.

Further, in the production method of the present invention, it is preferable to control the temperature of the mixture in the step (b) for more effectively suppressing the generation of aggregation and precipitation resulting from the reaction of the protein and the divalent metal ion. Specifically, the temperature is preferably 30° C. or higher, more preferably 40° C. or higher, and it is preferably 80° C. or lower, more preferably 70° C. or lower, further preferably 60° C. or lower. The step can be performed with a temperature of the mixture appropriately chosen from the aforementioned range. If the temperature is lower than 30° C. in the step (b), dispersibility of raw materials etc. is degraded, and thus operation efficiency is degraded. If the temperature is higher than 80° C., the raw materials may be denatured, and therefore such a temperature is not preferred.

In the present invention, as for the minimum value of the mixing ratio of the divalent metal salt, and the phosphoric acid salt and/or the organic acid salt, the mixing ratio of divalent metal ions derived from the divalent metal salt (calcium ions and/or magnesium ions), and phosphate ions and/or organic acid ions derived from the phosphoric acid salt and/or the organic acid salt [phosphate ions and/or organic acid ions (mol/l)]/[divalent metal ions (mol/l)]) is preferably larger than 0.5, more preferably 0.75 or larger, further preferably 1 or larger. The ratio is preferably 12 or smaller, more preferably 11 or smaller, further preferably 10 or smaller, still further preferably 9 or smaller, particularly preferably 8 or smaller. If the mixing ratio is smaller than 0.5, or larger than 12, the reaction of the divalent metal salt, and the phosphoric acid salt and/or the organic acid salt may become insufficient, and aggregation and precipitation may be caused after sterilization.

In the present invention, the "strainer" means a reticulated instrument used in order to remove solid components and insoluble components from a liquid or sol showing fluidity. The strainer is used for the purposes of prevention of contamination of the product with extraneous materials, and protection of instruments used in the production process such as emulsification machine and filling machine, and the shape thereof is not particularly limited. Further, mesh size of the strainer is not particularly limited so long as it is chosen so that the purposes of prevention of contamination of the product with extraneous materials, and protection of various instruments used in the production process are achieved. However, there can be used strainers having a mesh size of, for example, 18 mesh (opening: 850 μm), 22 mesh (opening: 710 μm), 26 mesh (opening: 600 μm), 30 mesh (opening: 500 μm), 36 mesh (opening: 425 μm), 40 mesh (opening: 405 μm), 42 mesh (opening: 355 μm), 50 mesh (opening: 300 μm), 60 mesh (opening: 250 μm), 70 mesh (opening: 212 μm), 83 mesh (opening: 180 μm), 100 mesh (opening: 150 μm), and 149 mesh (opening: 1000 μm). For the purposes of prevention of contamination of the product with extraneous materials, and protection of various instruments used in the production process, strainers having a mesh size of about 36 mesh (opening: 425 μm), 40 mesh (opening: 405 μm), 42 mesh (opening: 355 μm), 50 mesh (opening: 300 μm), 60 mesh (opening: 250 μm), or 70 mesh (opening: 212 μm) are preferably used.

The strainer is frequently disposed in piping (lines) connecting various instruments, and it is common to dispose it in each piping connecting various instruments such as mixing tank for mixing raw materials, emulsification machine, and filling machine. In usual production facilities, by connecting instruments (mixing tank, emulsification machine, filling machine, etc.) with piping, and transporting production liquids through it, processes such as mixing step, emulsification step, and filling step can be performed.

The "clogging of strainer" referred to in the present invention means a state that reticulated openings (mesh) of a strainer are clogged with fine particles generated in the production process of the composition, and the production liquids cannot be fed at all, or feeding rates of the production liquids are reduced so that the production liquids cannot be fed at desired flow rates expected from efficient cycle time of the production. As a result, there are caused such problems as that products cannot be produced, and production time is prolonged.

According to the production method of the present invention, such generation of clogging of a strainer as mentioned above can be avoided, therefore any problems concerning the production process are not raised also in the mixing step wherein raw materials are added, homogenization step using an emulsification machine, homogenizer, etc., and the step of filling into a container. Accordingly, the production time can be shortened, the composition can be produced with an efficient production schedule, and cost cut can be realized.

Further, in the liquid food composition obtained by the production method of the present invention, "sizes" of fine particles that causes clogging of strainer, aggregates generated after sterilization, etc. can be maintained to be small. Therefore, when the composition is ingested, the aforementioned particles and aggregates are in a state that they are easily digested with gastric acid and intestinal juice, and efficient absorption of minerals derived from the divalent metal salt, and nutritional components such as proteins can be attained.

The liquid food composition of the present invention may contain components other than the divalent metal salt, phosphoric acid salt and/or organic acid salt, protein, and water-soluble dietary fibers. For example, it may contain saccharides such as dextrin, fats and oils such as vegetable oil, animal fat, and fish oil, emulsifiers such as lecithin, lysolecithin, and polyglycerol fatty acid esters, dietary fibers, minerals other than calcium and magnesium, and/or mineral-containing yeast containing various minerals, vitamins, and flavoring agents. The order of the additions of these components are not particularly limited, but in order to efficiently advance the reaction of the divalent metal salt, the phosphoric acid salt and/or the organic acid salt, the protein, and the water-soluble dietary fibers, the other components and raw materials are preferably added after the steps (a) to (c) are completed. Further, after the produced liquid food composition is filled in a container, for example, pouches such as soft bag and aluminum pouch, paper pack, can, bottle, and so forth, sterilization can be performed with a retort sterilization machine. Further, a production liquid prepared by mixing the raw materials is sterilized with a continuous liquid sterilizer such as UHT sterilization machine, and then it can be aseptically filled in a container separately sterilized in advance.

The liquid food composition of the present invention can also be used as common food or drink. Since it enables easy ingestion of mineral ingredients such as calcium and magnesium together with major nutritional components such as proteins, it is especially preferably used for nutritional supplementary food, nutritional supplementary drink, and so forth. Further, since it can be a liquid food composition showing improved solidification ratio in the stomach etc., it can be used for nutritious foods, enteral nutritious foods, thick liquid diets, diets for patients with diabetes, kidney disease, etc., enteral nutrient preparations including those classified into drugs, and so forth utilizing the aforementioned advantage. The liquid food composition of the present invention can be ingested orally, by tube feeding, or the like, and ingestion method therefor is not particularly limited. However, it is preferably used as a thick liquid diet, and an enteral nutritious food or an enteral nutrient preparation, which is ingested by tube feeding.

The liquid food composition of the present invention can be a liquid food composition contained in a container, in which a predetermined volume (for example, not smaller than 100 ml and not larger than 500 ml) of the composition is filled in a container connectable with a nasogastric catheter or gastrostomy catheter.

The liquid food composition of the present invention can be used for elderly people, patients with diseases, preoperative or postoperative patients, and healthy subjects. It is particularly preferably used for those who have a disease or pathological condition, and require liquid foods (medical foods) or tube feeding. Examples of such disease or condition include insufficient biting power or swallowing power due to advanced age, reduction of deglutition power or dysphagia (late effect of cerebral stroke, amyotrophic lateral sclerosis, etc.), asitia due to central nerve disease (dementia disease etc.), asitia due to cancerous cachexia etc. (terminal cancer case etc.), stenosis from pharynx to cardia (pharyngeal cancer, esophageal cancer, gastric cardia cancer, etc.), disease for which elemental diet therapy is effective (Crohn's disease etc.), and gastroesophageal reflux diseases (including non-erosive gastroesophageal reflux disease, reflux esophagitis, and barrett esophagi).

In the present invention, the expression "A and/or B" is used to mean both A and B, or either one of A and B, unless especially indicated.

EXAMPLES

Hereafter, the present invention will be specifically explained with reference to the following examples and comparative example. However, the present invention is not limited by them.

(Example 1) <Addition of Phosphoric Acid Salt after Addition of Magnesium Salt>

Magnesium carbonate (22 g) was added to warm water adjusted to 50° C. (Mg ions, 65 mmol/l), and the mixture was stirred at 370 rpm. Then, potassium dihydrogenphosphate (23 g, 42 mmol/l of phosphate ions) and sodium dihydrogenphosphate dodecahydrate (22 g, 15 mmol/l of phosphate ions) were added to the solution containing the magnesium salt, and they were mixed by stirring. Further, 10 minutes after the time of the addition of the phosphoric acid salts (pH of the mixture was 6.8), 10 g of soybean proteins were added, sodium alginate (20 g) was further added, and the final volume of the mixture was made to be 4000 ml. Then, the total volume of the mixture was filtered through a metal mesh (60 mesh sieve for JIS test, opening 250 μm, diameter 75 mm), and weight of the residue remained on the mesh was measured after drying at 80° C. for 1 hour [(Residue weight)=(Mesh weight including residue after drying)−(Mesh weight)]. The weight of the residue was 160 mg, thus the weight after the filtration through the mesh reduced compared with that observed in Comparative Example 1, and mesh penetration property of the composition was favorable (Table 1). pH was measured with a pH meter, D-53 (HORIBA), which was calibrated at three points in advance using standard buffer solutions (pH 4.01±0.02, pH 6.86±0.02, and pH 9.18±0.02, Nacalai Tesque), and disposed in the reaction vessel, at a temperature of about 50° C. The same shall apply to the following examples.

(Comparative Example 1) <Addition of Magnesium Salt after Addition of Phosphoric Acid Salt>

Potassium dihydrogenphosphate (23 g, 42 mmol/l of phosphate ions) and sodium dihydrogenphosphate dodecahydrate (22 g, 15 mmol/l of phosphate ions) were added to warm water adjusted to 50° C., and the mixture was stirred at 370 rpm. Then, magnesium carbonate (22 g, 65 mmol/l of Mg ions) was added to the solution containing the phosphoric acid salts, and the experiment was performed thereafter in the same manner as that of Example 1. At the time of the addition of the soybean proteins, pH of the mixture was 6.8. Then, as in Example 1, the total volume of the mixture was filtered through a metal mesh (60 mesh sieve for JIS test, opening 250 μm, diameter 75 mm), and weight of the residue remained on the mesh was measured after drying at 80° C. for 1 hour. In Comparative Example 1, the weight of the residue was 250 mg, and clogging of the mesh was caused. Therefore, the mesh penetration property of the composition was markedly inferior to that observed in Example 1 (Table 1).

TABLE 1

|  | Order of addition | pH at the time of addition of proteins | Mesh (250 μm) residue weight |
|---|---|---|---|
| Example 1 | Mg salt -> phosphoric acid salt | pH 6.8 | 160 mg |
| Comparative Example 1 | Phosphoric acid salt -> Mg salt | pH 6.8 | 250 mg |

(Example 2) <Addition of Phosphoric Acid Salt after Addition of Magnesium Salt>

In the same manner as that of Example 1, a solution containing a magnesium salt (Mg ions, 65 mmol/l) and phosphoric acid salts (phosphate ions, 57 mmol/l) was prepared. Further, 60 minutes after the time of the addition of the phosphoric acid salts (pH of the mixture was 7.5), sodium alginate (20 g) was added, soybean proteins (10 g) were further added, and then the final volume of the mixture was made to be 4000 ml. Then, the total volume of the mixture was filtered through a metal mesh (42 mesh sieve for JIS test, opening 355 μm, diameter 75 mm), and weight of the residue remained on the mesh was measured after drying at 80° C. for 1 hour. The weight of the residue was 30 mg, and reduced compared with that observed in Comparative Example 2, and the total volume of the prepared composition could be filtered (Table 2).

(Comparative Example 2) <Addition of Magnesium Salt after Addition of Phosphoric Acid Salt>

In the same manner as that of Comparative Example 1, a solution containing phosphoric acid salts (phosphate ions, 57 mmol/l) and a magnesium salt (Mg ions, 65 mmol/l) was prepared. Further, 60 minutes after the time of the addition of the magnesium salt (pH of the mixture was 7.5), sodium alginate (20 g) was added to the solution, soybean proteins (10 g) were further added, and the final volume of the mixture was made to be 4000 ml. Then, the total volume of the mixture was filtered through a metal mesh in the same manner as that of Example 2. As a result, weight of the residue was 270 mg. In Comparative Example 2, the mesh was clogged during the filtration, and thus the penetration property of the composition was markedly degraded (Table 2).

TABLE 2

|  | Order of addition | pH at the time of addition of proteins | Mesh (355 μm) residue weight |
|---|---|---|---|
| Example 2 | Mg salt -> phosphoric acid salt | pH 7.5 | 30 mg |
| Comparative Example 2 | Phosphoric acid salt -> Mg salt | pH 7.5 | 270 mg |

Example 3

Magnesium carbonate (5.5 g, 16 mmol/l of Mg ions) and calcium carbonate (7.6 g, 19 mmol/l of Ca ions) were suspended in a small volume of warm water, the suspension was added to warm water adjusted to 60° C., and the mixture was stirred. Then, potassium dihydrogenphosphate (5.8 g, 11 mmol/l of phosphate ions) and sodium dihydrogenphosphate dodecahydrate (5.5 g, 4 mmol/l of phosphate ions) were dissolved in a small volume of warm water, and the solution was added to the solution containing the magnesium salt. Mixing by stirring was continued, and when pH of the mixture reached 7.1, proteins (180 g) were added. Sodium alginate (40 g) was further added, the other raw materials were added in amounts mentioned in Table 3, and the final volume of the mixture was made to be 4000 ml. Then, the total volume of the mixture was filtered through a metal mesh (40 mesh, opening 405 μm, diameter 75 mm), and weight of the residue remained on the mesh was measured after drying at 80° C. for 1 hour. The weight of the residue observed in Example 3 was 20 mg, and the total volume of the mixture could be filtered without causing clogging in the mesh (Table 4).

Comparative Example 3

Potassium dihydrogenphosphate (5.8 g, 11 mmol/l of phosphate ions) and sodium dihydrogenphosphate dodecahydrate (5.5 g, 4 mmol/l of phosphate ions) were dissolved in a small volume of warm water, the solution was added to warm water adjusted to 60° C., and the mixture was stirred. Then, magnesium carbonate (5.5 g, 16 mmol/l of Mg ions) and calcium carbonate (7.6 g, 19 mmol/l of Ca ions) were suspended in a small volume of warm water, and the suspension was added to the solution containing phosphoric acid salts. The operations were performed thereafter by using the same method and materials as those mentioned in Example 3. At the time of the addition of the soybean proteins, pH of the mixture was 7.1. The prepared mixture was filtered through a metal mesh (40 mesh, opening 405 μm, diameter 75 mm). However, in Comparative Example 3, clogging was caused in the mesh during the filtration, and the total volume of the mixture could not be filtered. The weight of the residue estimated from the weight of the residue on the mesh obtained by filtration of a part of the prepared mixture was 340 mg (Table 4).

TABLE 3

| Material | Added weight (g) |
| --- | --- |
| Magnesium carbonate | 5.5 |
| Calcium carbonate | 7.6 |
| Potassium dihydrogenphosphate | 5.8 |
| Sodium dihydrogenphosphate | 5.5 |
| Soybean proteins | 180 |
| Water-soluble dietary fibers (Na alginate) | 40 |
| Dextrin | 480 |
| Fats and oils | 140 |
| Emulsifier (lysolecithin) | 14 |
| Minerals and vitamins | 20 |
| Warm water | 3102 |
| Final volume (ml) | 4000 |

TABLE 4

| | Order of addition | pH at the time of addition of proteins | Mesh (355 μm) residue weight |
| --- | --- | --- | --- |
| Example 3 | Mg salt -> phosphoric acid salt | pH 7.1 | 20 mg |
| Comparative Example 3 | Phosphoric acid salt -> Mg salt | pH 7.1 | 340 mg |

Example 4

<Test for Confirming Solidification Ratio>
(1) Artificial gastric juice (Japanese Pharmacopoeia, Disintegration test, 1st fluid, precisely, a solution prepared by dissolving 2.0 g of sodium chloride in 7.0 mL of hydrochloric acid and water to make 1000 mL, this solution is clear and colorless, and has a pH of about 1.2) kept at 37° C. in an amount of 20 g was added to a 50 ml volume plastic tube.
(2) The liquid food composition (10 g, 25° C.) was added to the artificial gastric juice, and weight of the plastic tube containing the artificial gastric juice and the liquid food composition was measured (this is used as [weight of tube before filtration]).
(3) The content in the plastic tube was gently stirred by using "HL-2000 HybriLinker" (UVP Laboratory Products). More precisely, the tube was fixed with the immobilization device in the chamber, the motor control mode was adjusted to the minimum level by switching the Motor Control dial of the apparatus to the indication of "MIN", and then the content was stirred under the conditions of 37° C. for 2 minutes and 30 seconds.
(4) The solid matter was subjected to suction filtration on a nylon screen (40 mesh, SOGO LABORATORY GLASS WORKS) to remove the liquid portion, the residue was placed on paper towel or the like together with the nylon screen to remove excessive moisture over 2 minutes, and weight of the solid matter including the nylon screen was measured (it is used as [weight of solid matter after filtration]). Further, after the content liquid in the tube was emptied, moisture remaining in the tube was removed, and weight of the plastic tube was measured (it is used as [Weight after filtration]).
(5) The solid matter remained on the nylon screen was confirmed, and the solidification ratio was calculated in accordance with the equation (1).

[Equation 1]

$$\text{Solidification ratio} = \frac{(\text{Weight of solid matter after filtration}) - (\text{Weight of nylon screen})}{(\text{Weight of tube before filtration}) - (\text{Weight after filtration}) - (\text{Weight of artificial gastric juice})} \times 100 \quad \text{Equation (1)}$$

<Production of Liquid Food Composition>
Magnesium carbonate (5.5 g, 16 mmol/l of Mg ions) and calcium carbonate (7.6 g, 19 mmol/l of Ca ions) were added to warm water, and the mixture was stirred. Then, potassium dihydrogenphosphate (5.8 g, 11 mmol/l of phosphate ions) and sodium dihydrogenphosphate dodecahydrate (5.5 g, 4 mmol/l of phosphate ions) were added to the solution containing the divalent metal salt to prepare a mixture containing the divalent metal salt and the phosphoric acid salts. Mixing by stirring was continued, and when pH of the mixture reached 6.2 (condition 1), 6.8 (condition 2), 7.2 (condition 3), or 9.5 (condition 4), proteins (180 g) were added. Sodium alginate (40 g) was further added, the other raw materials were added in amounts mentioned in Table 3, and the final volume of the mixture was made to be 4000 ml. Then, the liquid food composition was subjected to a homogenization treatment using a Manton Gaulin type high pressure homogenizer (Rannie 2000, APV) at 20 MPa (1st time), and 48 MPa (2nd time), and then subjected to sterilization (F value, 8) in a retort sterilization machine. The evaluation results for presence or absence of aggregates after the sterilization treatment, and the evaluation results for the solidification ratios of the liquid food compositions produced with the aforementioned conditions are shown in Table 5. As a result, for all the conditions, presence of aggregates was not observed in the liquid food compositions, the solidification ratios were 60% or higher, and the liquid food compositions favorably solidified.

Comparative Example 4

Magnesium carbonate (5.5 g, 16 mmol/l of Mg ions) and calcium carbonate (7.6 g, 19 mmol/l of Ca ions) were added to warm water, and the mixture was stirred. Then, phosphoric acid (11 g, 28 mmol/l of phosphate ions) was added to the aqueous solution containing the divalent metal salt to prepare a mixture containing the divalent metal salt and phosphoric acid. Mixing by stirring was continued, and when pH of the mixture reached 3.5, proteins (180 g) were added. When sodium alginate (40 g) was then added, viscosity of the mixture sharply increased. The viscosity of the mixture exceeded 1000 cP, and the physical properties of the liquid food composition as liquid were degraded. Further, presence or absence of aggregates after the sterilization and the solidification ratio were evaluated. As a result, a lot of aggregates were observed, and the compositions had already thickened, and showed physical properties unsuitable for the evaluation of solidification ratio (Table 5). Viscosities of the liquid food compositions were measured with a "Brookfield" type viscometer (TOKIMEC). More precisely, a measurement sample was put into a glass container having an internal diameter of 60 mm, the measurement was performed 3 times with the conditions of a liquid temperature of 25° C., rotor No. 2, revolution number of 60 rpm, and retention time of 30 seconds, and the average of the results was used as a measured value (viscosity).

Comparative Example 5

Magnesium carbonate (5.5 g, 16 mmol/l of Mg ions) and calcium carbonate (7.6 g, 19 mmol/l of Ca ions) were added to warm water, and the mixture was stirred. Then, potassium dihydrogenphosphate (5.8 g, 11 mmol/l of phosphate ions) and sodium dihydrogenphosphate dodecahydrate (5.5 g, 4 mmol/l of phosphate ions) were added to the aqueous solution containing the divalent metal salts to prepare a mixture containing the divalent metal salts and phosphoric acid salts. Mixing by stirring was continued, and when pH of the mixture reached 6.0, proteins (180 g) were added. The operation was performed thereafter in the same manner as that of Example 4 to produce a liquid food composition. Further, presence or absence of aggregates after the sterilization and the solidification ratio were evaluated. As a result, aggregates were observed in the liquid food composition, and the solidification ratio was as low as 47% (Table 5).

TABLE 6

|  | Condition 1 | Condition 2 | Condition 3 | Condition 4 |
|---|---|---|---|---|
| Condition | 20° C. | 30° C. | 70° C. | 80° C. |
| Amount of residue on mesh | Not larger than 75 mg | Not larger than 50 mg | Not larger than 50 mg | Not larger than 50 mg |

Example 6

To 3.4 g of magnesium carbonate (10 mmol/l of Mg ions), potassium dihydrogenphosphate was added in an amount of 2.7 g (condition 1, 5 mmol/l of phosphate ions), 5.4 g (condition 2, 10 mmol/l of phosphate ions), 32.4 g (condition 3, 60 mmol/l of phosphate ions), or 65.3 g (condition 4, 120 mmol/l of phosphate ions) to prepare mixtures containing the divalent metal salt and the phosphoric acid salt. Mixing by stirring was continued, and when pH of the mixtures exceeded 7.1, proteins (180 g) were added. The other raw materials were added in amounts mentioned in Table 3, and the final volume of the mixture was made to be 4000 ml. Then, each liquid food composition was subjected to a homogenization treatment using a high pressure homogenizer, and then subjected to retort sterilization. The evaluation results for aggregates after the sterilization treatment, and the evaluation results for the solidification ratio for the liquid food compositions produced with the aforementioned conditions are shown in Table 7. As a result, for all the conditions, presence of aggregates was not observed in the liquid food compositions, the solidification ratio was 60% or higher, and the liquid food compositions favorably solidified.

Comparative Example 6

A liquid food composition was produced by the method described in Example 6 by using 3.4 g of magnesium carbonate (10 mmol/l of Mg ions) without adding the

TABLE 5

|  | Comparative Example 4 | Comparative Example 5 | Example 4 | | | |
|---|---|---|---|---|---|---|
|  |  |  | Condition 1 | Condition 2 | Condition 3 | Condition 4 |
| Condition | pH 3.5 | pH 6.0 | pH 6.2 | pH 6.8 | pH 7.2 | pH 9.5 |
| Presence or absence of aggregates | Present | Present | Slightly Present | Absent | Absent | Absent |
| Solidification ratio | — | 47% | 60% | 65% | 70% | 68% |

Example 5

In the same manners as those described in Example 3, liquid food compositions were produced with the temperature conditions of 20° C. (condition 1), 30° C. (condition 2), 70° C. (condition 3), and 80° C. (condition 4), and evaluated. The results obtained after the total volume of each composition was filtered through a metal mesh (36 mesh sieve for JIS test, opening 425 μm, diameter 75 mm) are shown in Table 6. As a result, although the residue weight was not larger than 75 mg with the condition 1, the residue weights observed for the compositions produced with the conditions 2 to 4 were not larger than 50 mg, and the whole volumes of them could be filtered without causing clogging in the mesh.

phosphoric acid salt (0 mol/l of phosphate ion). Presence or absence of aggregates after sterilization and the solidification ratio were evaluated. As a result, a lot of aggregates were observed in the liquid food composition, and the solidification ratio was as low as 45% (Table 7).

TABLE 7

| | | Example 6 | | | |
|---|---|---|---|---|---|
| Condition | Comparative Example 6 | Condition 1 | Condition 2 | Condition 3 | Condition 4 |
| Mixing ratio (phosphate ion/metal salt ion) | 0 | 0.5 | 1 | 6 | 12 |

TABLE 7-continued

| | | Example 6 | | | |
|---|---|---|---|---|---|
| Condition | Comparative Example 6 | Condition 1 | Condition 2 | Condition 3 | Condition 4 |
| Presence or absence of aggregate | Many | None | None | None | None |
| Semi-solidification ratio | 45% | 60% | 63% | 65% | 60% |

The invention claimed is:

1. A method for producing a liquid food composition, the method comprising:
   mixing a divalent metal salt with a solvent to obtain a first mixture, wherein the divalent metal salt comprises at least one of a calcium compound and a magnesium compound;
   adding to the first mixture at least one of a phosphoric acid salt and an organic acid salt to obtain a second mixture;
   mixing the second mixture such that the second mixture has a pH of 6.2 to 9.5;
   adding to the second mixture having a pH of 6.2 to 9.5 a protein to obtain a third mixture, wherein the protein is mixed with the second mixture in a proportion of 0.25 to 20 g/100 ml of the second mixture; and
   mixing water-soluble dietary fibers with the solvent, the first mixture, the second mixture, or the third mixture, thereby obtaining a liquid food composition comprising the divalent metal salt, at least one of the phosphoric acid salt and the organic acid salt, the protein, and the water-soluble dietary fibers,
   wherein the water-soluble dietary fibers consist of at least one type of fiber selected from the group consisting of alginic acid, a salt of the alginic acid, and pectin;
   wherein the liquid food composition has a solidification ratio higher than 51% at a pH not lower than 5.5, and
   wherein the divalent metal salt is mixed such that an amount of the divalent metal salt in terms of divalent metal ions in the obtained liquid food composition is 1 mmol/l or more.

2. The method according to claim 1, wherein the protein is mixed with the second mixture at a temperature of from 30 to 80° C.

3. The method according to claim 1, wherein the liquid food composition includes comprises i) phosphate ions and/or organic acid ions derived from the phosphoric acid salt and/or the organic acid salt, and ii) divalent metal ions derived from the divalent metal salt at a mole ratio, i)/ii), of from 0.5 to 12.

4. The method according to claim 2, wherein the liquid food composition comprises i) phosphate ions and/or organic acid ions derived from the phosphoric acid salt and/or the organic acid salt, and ii) divalent metal ions derived from the divalent metal salt at a mole ratio, i)/ii), of from 0.5 to 12.

5. The method according to claim 1, wherein the liquid food composition comprises i) phosphate ions and organic acid ions derived from the phosphoric acid salt and the organic acid salt, and ii) divalent metal ions derived from the divalent metal salt at a mole ratio, i)/ii), of from 0.5 to 12.

6. The method according to claim 1, wherein the protein is mixed with the second mixture in a proportion of 1.0 to 7.5 g/100 ml of the second mixture.

7. The method according to claim 3, wherein the protein is mixed with the second mixture in a proportion of 2.0 to 5.0 g/100 ml of the second mixture.

8. The method according to claim 1, wherein the first mixture is mixed with a phosphoric acid salt and an organic acid salt to obtain the second mixture.

9. The method according to claim 8, wherein the organic acid salt comprises a citric acid salt.

10. The method according to claim 1, wherein the first mixture is mixed with an organic acid salt comprising a citric acid salt.

11. The method according to claim 1, wherein the mixing of the second mixture is performed such that the second mixture has a pH of 6.8 to 9.0.

12. The method according to claim 1, wherein the obtained liquid food composition is an enteral nutritious food or an enteral nutrient preparation, which is ingested by tube feeding.

13. The method according to claim 1, wherein the divalent metal salt is mixed such that an amount of the divalent metal salt in terms of divalent metal ions in the obtained liquid food composition is 10 mmol/l or more.

14. The method according to claim 1, wherein at least one of the phosphoric acid salt and the organic acid salt is mixed such that an amount of at least one of the phosphoric acid salt and the organic acid salt in terms of phosphate ions and/or organic acid ions in the obtained liquid food composition is 2.5 mmol/l or larger.

15. The method according to claim 1, wherein at least one of the phosphoric acid salt and the organic acid salt is mixed such that an amount of at least one of the phosphoric acid salt and the organic acid salt in terms of phosphate ions and/or organic acid ions in the obtained liquid food composition is 5 mmol/l or larger.

16. The method according to claim 1, wherein the water-soluble dietary fibers are mixed such that an amount of the water-soluble dietary fibers is 0.3 g/100 ml liquid food composition or larger.

* * * * *